(12) United States Patent
Yao et al.

(10) Patent No.: US 7,030,201 B2
(45) Date of Patent: Apr. 18, 2006

(54) BOTTOM ANTIREFLECTIVE COATINGS

(75) Inventors: Huirong Yao, Plainsboro, NJ (US);
Shuji Ding-Lee, Branchburg, NJ (US);
Hengpeng Wu, Hillsborough, NJ (US);
Zhong Xiang, Somerset, NJ (US)

(73) Assignee: AZ Electronic Materials USA Corp.,
Somerville, NJ (US)

( * ) Notice: Subject to any disclaimer, the term of this patent is extended or adjusted under 35 U.S.C. 154(b) by 89 days.

(21) Appl. No.: 10/721,883

(22) Filed: Nov. 26, 2003

(65) Prior Publication Data

US 2005/0112494 A1    May 26, 2005

(51) Int. Cl.
*C08F 126/06* (2006.01)
*C08F 226/06* (2006.01)
*C08F 122/40* (2006.01)
*C08F 4/44* (2006.01)
*C07C 321/00* (2006.01)

(52) U.S. Cl. ............... 526/260; 526/262; 526/304; 525/123; 525/326.7; 525/326.8; 525/327.1; 525/328.2; 540/525; 546/142; 546/183; 546/237; 546/296; 544/175; 548/479; 548/547; 564/158; 564/159; 564/162

(58) Field of Classification Search ........ 526/260, 526/262, 304; 525/123, 326.7, 326.8, 327.1, 525/328.2; 548/479, 547; 546/142, 183, 546/237, 296; 564/158, 159, 162; 544/175; 540/526, 525
See application file for complete search history.

(56) References Cited

U.S. PATENT DOCUMENTS

| | | | |
|---|---|---|---|
| 4,079,041 A * | 3/1978 | Baumann et al. ............ 526/258 |
| 4,247,660 A * | 1/1981 | Zweifel et al. .............. 525/61 |
| 4,532,332 A * | 7/1985 | Muller ....................... 548/473 |
| 5,424,364 A | 6/1995 | Simms et al. |
| 5,919,599 A | 7/1999 | Meador et al. |
| 6,156,479 A | 12/2000 | Meador et al. |
| 6,369,249 B1 | 4/2002 | Lele et al. |
| 6,730,763 B1 * | 5/2004 | Okazaki et al. ............. 526/262 |
| 2002/0156148 A1 | 10/2002 | Arase et al. |
| 2003/0004283 A1 | 1/2003 | Puligadda et al. |

FOREIGN PATENT DOCUMENTS

EP    0 922 715 A2    6/1999

OTHER PUBLICATIONS

English language abstract of JP37009212, published 19620725.
Notification of Transmittal of International Search Report and the Written Opinion of the International Searching Authority (Form PCT/ISA/220) for PCT/IB2004/004412.
International Search Report (Form PCT/ISA/210) for PCT/IB2004/004412.
Written Opinion of the International Search Authority (Form PCT/ISA/237) for PCT/IB2004/004412.

* cited by examiner

*Primary Examiner*—Richard L. Schilling
(74) *Attorney, Agent, or Firm*—Alan P. Kass

(57) ABSTRACT

The present invention relates to bottom antireflective coating compositions and polymers useful in making such compositions.

22 Claims, No Drawings

BOTTOM ANTIREFLECTIVE COATINGS

BACKGROUND OF THE INVENTION

The present invention relates to bottom antireflective coating compositions, polymers useful in making such compositions, and their use in image processing by forming a thin layer between a reflective substrate and a photoresist coating. Such compositions are especially useful in the fabrication of semiconductor devices by photolithographic techniques and provide improved etch-rate for such bottom antireflective coatings.

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The baked coated surface of the substrate is next subjected to an image-wise exposure to radiation.

This radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the photoresist.

The trend towards the miniaturization of semiconductor devices has lead to the use of sophisticated multilevel systems to overcome difficulties associated with such miniaturization. The use of highly absorbing anti-reflective coatings in photolithography is a simpler approach to diminish the problems that result from back reflection of light from highly reflective substrates. Two deleterious effects of back reflectivity are thin film interference and reflective notching. Thin film interference results in changes in critical linewidth dimensions caused by variations in the total light intensity in the resist film as the thickness of the resist changes. Variations of linewidth are proportional to the swing ratio (S) and therefore must be minimized for better linewidth control. Swing ratio is defined as $$S=4(R_a R_b)^{1/2} e^{-\alpha D}$$

where $R_a$ is the reflectivity at the resist/air or resist/top coat interface,
where $R_b$ is the reflectivity at the resist/substrate interface,
where $\alpha$ is the resist optical absorption coefficient, and
D is the film thickness.

Bottom anti-reflective coatings function by absorbing the radiation used for exposing the photoresist, thus reducing $R_b$ and thereby reducing the swing ratio. Reflective notching becomes severe as the photoresist is patterned over substrates containing topographical features, which scatter light through the photoresist film, leading to linewidth variations, and in the extreme case, forming regions with complete resist loss. Similarly, dyed top anti-reflective coatings reduce the swing ratio by reducing $R_a$, where the coating has the optimal values for refractive index and absorption characteristics, such as absorbing wavelength and intensity.

U.S. Pat. No. 6,156,479 discloses anti-reflective coating compositions prepared from certain acrylic polymers and copolymers reacted with a non-polycyclic carboxylic acid or phenolic dye using glycidyl methacrylate where the reaction opens the epoxy ring to form a hydroxyester linkage. U.S. Patent Application Publication No. 2003/0004283 (equivalent WO 02/099531) discloses anti-reflective coating compositions where chromophores are physically mixed in the composition or react with epoxide rings present in the polymer(s) of the composition. U.S. Patent Application Publication No. 2002/0156148 discloses maleimide copolymerization with methacrylates. JP 37009212 (25 Jul. 1962), EP 922 715, and U.S. Pat. No. 6,369,249 disclose comparative syntheses of N-acetyl acrylamide and (co)polymerization reactions thereof.

SUMMARY OF THE INVENTION

The present invention relates to a polymer comprising at least one repeating unit represented by formula (I) or (II)

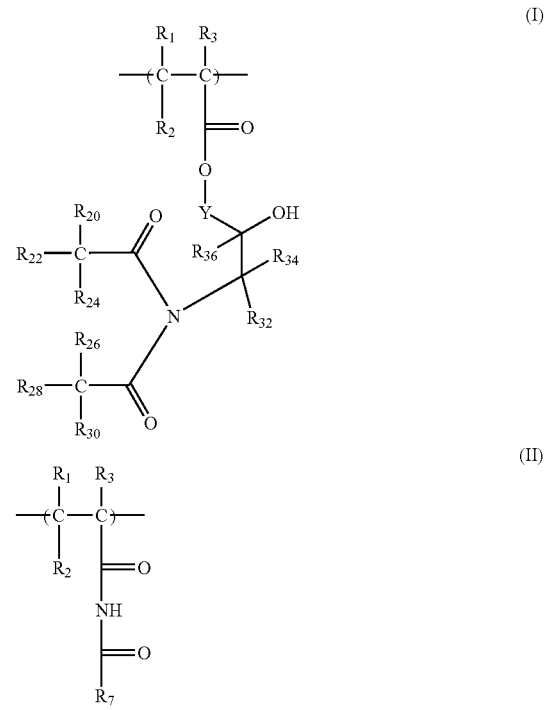

where $R_1$, $R_2$, and $R_3$ are each independently selected from hydrogen or alkyl; $R_7$ is alkyl or aryl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The polymer can further comprise an additional monomer such as those selected from optionally substituted acrylic esters, optionally substituted acrylic acids, optionally substituted methacrylic esters, optionally substituted methacrylic acids, optionally substituted acrylamides, optionally substituted methacrylamides, optionally substituted allyl compounds, optionally substituted styrenes, optionally substituted hydroxystyrene, optionally substituted hydroxyisopropylstyrene, optionally substituted methylstyrene, optionally substituted hydroxymethylstyrene, optionally substituted hydroxyl-α-methylstyrene, optionally substituted vinyl ethers, optionally substituted vinyl esters, optionally substituted crotonic acids, optionally substituted crotonic acid esters, optionally substituted maleic anhydride, optionally substituted dialkyl itaconates, optionally substituted monoalkyl or dialkyl esters of maleic acid or fumaric acid, and mixtures thereof. When the polymer comprises a repeating unit represented by formula (II), it is preferable that at least one of the additional monomers contains at least one pendent hydroxyl group, more preferably the monomer is selected from optionally substituted methacrylic esters. The invention also relates to a method of making the polymer.

The invention also relates to an antireflective coating composition which comprises the polymer of the present invention and at least one crosslinking agent.

The invention also relates to a compound having the formula

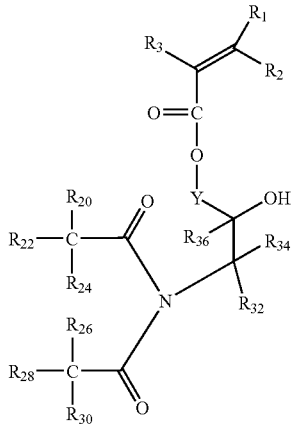

(V)

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The invention also relates to a method for making the compound of formula (V) which involves reacting a compound of formula (IB)

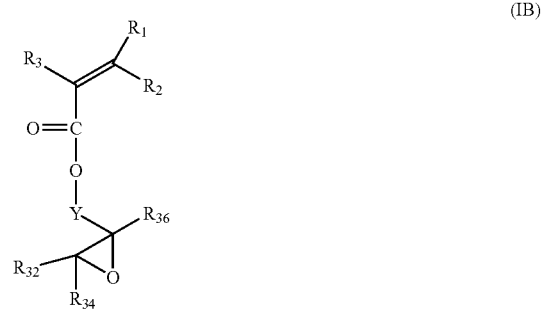

(IB)

with a compound of formula (IA)

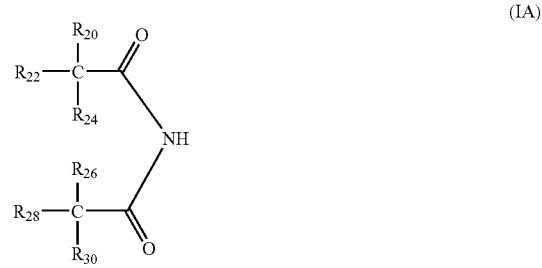

(IA)

in the presence of a catalyst, where Y, $R_1$, $R_2$, $R_3$, $R_{20}$, $R_{22}$, $R_{24}$, $R_{26}$, $R_{28}$, $R_{30}$, $R_{32}$, $R_{34}$, and $R_{36}$ are defined above, and separating the compound of formula (V) from the reaction mixture.

The invention also relates to a method of making a compound having formula (III) comprising

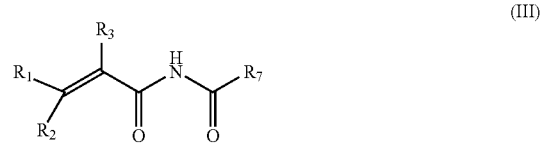

(III)

reacting a compound having formula (IIa) with a compound having formula (IIIb)

(IIIa)

-continued

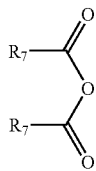
(IIIb)

where $R_1$, $R_2$, and $R_3$ are each independently selected from hydrogen or alkyl; and $R_7$ is alkyl or aryl, in the presence of a catalyst and separating the compound of formula (III) from the reaction mixture.

The invention also relates to a method of making a polymer having a repeating unit of formula (I) which comprises reacting a vinyl polymer or copolymer containing from about 40 to about 100 mol % of an epoxy substituent and an imide in the presence of a catalyst and separating the polymer having the repeating unit having formula (I) from the reaction mixture. The vinyl polymer or copolymer comprises at least one repeating unit having the formula

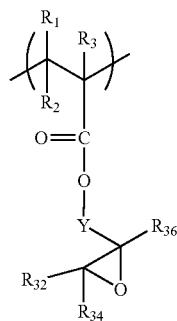

and the imide can be

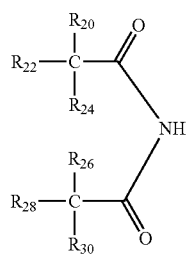
(IA)

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from alkyl, aryl, aralkyl, or 5-, 6-, or 7-membered heterocyclic ring containing at least one heteroatom selected from nitrogen, oxygen or sulfur; Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The invention also relates to a process for forming an image comprising a) coating and baking a substrate with the antireflective coating composition of the present invention; b) coating and baking a photoresist film on top of the antireflective coating; c) imagewise exposing the photoresist; d) developing an image in the photoresist; e) optionally, baking the substrate after the exposing step. The exposed anti-reflective film can then be dry etched, usually in an oxygen-containing plasma, with the photoresist pattern acting as an etch mask.

DETAILED DESCRIPTION OF THE INVENTION

The present invention relates to a polymer comprising at least one repeating unit represented by formula (I) or (II)

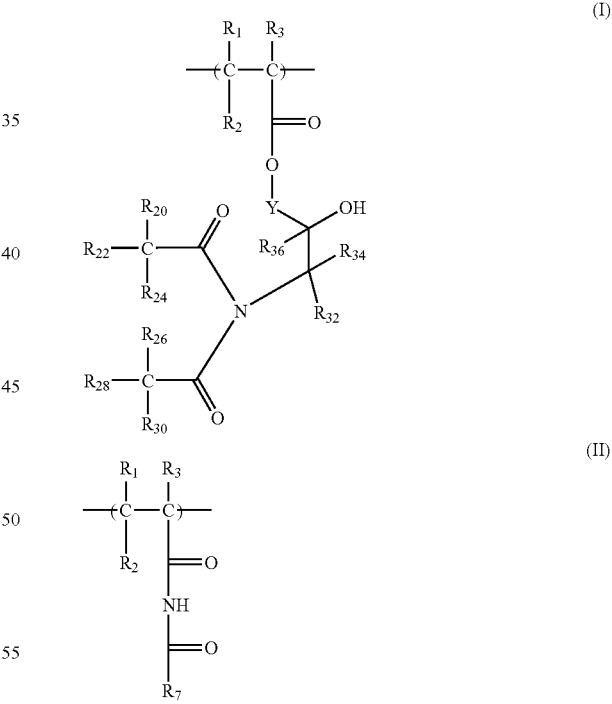

where $R_1$, $R_2$, and $R_3$ are each independently selected from hydrogen or alkyl; $R_7$ is alkyl or aryl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The polymer can further comprise an additional monomer such as those selected from optionally substituted acrylic esters, optionally substituted acrylic acids, optionally substituted methacrylic esters, optionally substituted methacrylic acids, optionally substituted acrylamides, optionally substituted methacrylamides, optionally substituted allyl compounds, optionally substituted styrenes, optionally substituted hydroxystyrene, optionally substituted hydroxyisopropylstyrene, optionally substituted methylstyrene, optionally substituted hydroxymethylstyrene, optionally substituted hydroxyl-α-methylstyrene, optionally substituted vinyl ethers, optionally substituted vinyl esters, optionally substituted crotonic acids, optionally substituted crotonic acid esters, optionally substituted maleic anhydride, optionally substituted dialkyl itaconates, optionally substituted monoalkyl or dialkyl esters of maleic acid or fumaric acid, and mixtures thereof. When the polymer comprises a repeating unit represented by formula (II), it is preferable that at least one of the additional monomers contains at least one pendent hydroxyl group, more preferably the monomer is selected from optionally substituted methacrylic esters. The invention also relates to a method of making the polymer.

The invention also relates to an antireflective coating composition which comprises the polymer of the present invention and at least one crosslinking agent.

The invention also relates to a compound having the formula

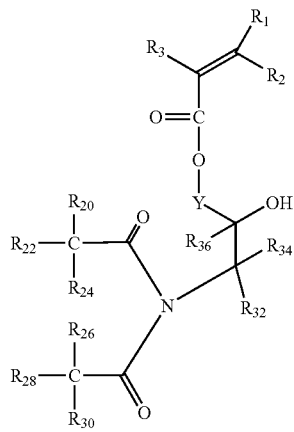

(V)

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The invention also relates to a method for making the compound of formula (V) which involves reacting a compound of formula (IB)

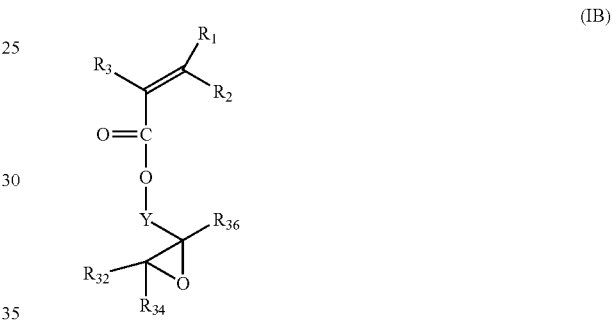

with a compound of formula (IA)

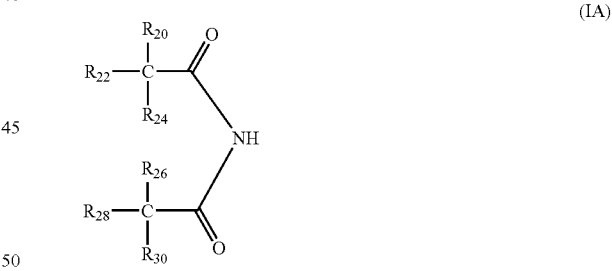

in the presence of a catalyst, where Y, $R_1$, $R_2$, $R_3$, $R_{20}$, $R_{22}$, $R_{24}$, $R_{26}$, $R_{28}$, $R_{30}$; $R_{32}$, $R_{34}$, and $R_{36}$ are defined above, and separating the compound of formula (V) from the reaction mixture.

The invention also relates to a method of making a compound having formula (III) comprising

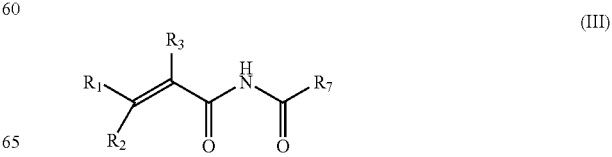

reacting a compound having formula (IIIa) with a compound having formula (IIIb)

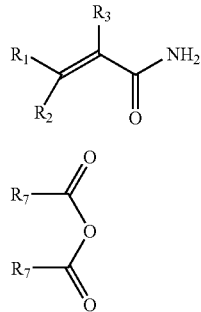

where $R_1$, $R_2$, and $R_3$ are each independently selected from hydrogen or alkyl; and $R_7$ is alkyl or aryl, in the presence of a catalyst and separating the compound of formula (III) from the reaction mixture.

The invention also relates to a method of making a polymer having a repeating unit having formula (I) which comprises reacting a vinyl polymer or copolymer containing from about 40 to about 100 mol % of an epoxy substituent and an imide in the presence of a catalyst and separating the polymer having the repeating unit having formula (I) from the reaction mixture. The vinyl polymer or copolymer comprises at least one repeating unit having the formula

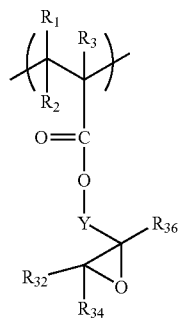

and the imide is

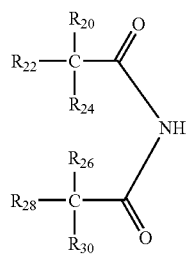

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

For the polymer where at least one repeating unit is represented by formula (I), for example, when $R_{24}$ and $R_{26}$ taken together form a direct bond and $R_{20}$, $R_{22}$, $R_{28}$, and $R_{30}$ are as defined above, the pendent moiety is succinimide. When $R_{24}$ and $R_{26}$ taken together form —$(CH_2)_{n1}(O)_{n2}(CH_2)_{n3}$—, n2 is 0 and n1+n2+n3=1, and $R_{20}$, $R_{22}$, $R_{28}$, and $R_{30}$ are as defined above, the pendent moiety is glutarimide. When $R_{24}$ and $R_{26}$ taken together form —$(CH_2)_{n1}(O)_{n2}(CH_2)_{n3}$—, n2 is 1 and n1+n2+n3=1, the pendent group is 3,5-morpholinedione. When $R_{24}$ and $R_{26}$ taken together with the carbon atoms to which they are attached form a carbocyclic ring and $R_{20}$, $R_{22}$, $R_{28}$, and $R_{30}$ are as defined above, the pendent moiety can be, for example, phthalimide or naphthalimide.

Examples of the linear or branched alkylene group can have from 1 to 20 carbon atoms and include such as, for example, methylene, ethylene, propylene and octylene groups.

Examples of the monocyclic cycloalkylene group can have from 4 to 12 carbon atoms, and include such as, for example, cyclopentylene and cyclohexylene groups, and the polycyclic cycloalkylene group can have from 5 to 50 carbon atoms and include such as, for example, 7-oxabicyclo[2,2,1]heptylene, norbornylene, adamantylene, and divalent diamondoids having the formula $C_{4n+6}H_{4n+10}$, where n is 2 to 11 (wherein the diamondoid has the general formula of $C_{4n+6}H_{4n+12}$; see, for example, Marchand, Alan P., *Science*, 299, 52 (3 Jan. 2003)).

Examples of the arylene group include monocyclic and polycyclic groups such as, for example, phenylene, naphthylene, biphenyl-4,4'-diyl, biphenyl-3,3'-diyl, and biphenyl-3,4'-diyl groups.

Examples of the linear or branched alkenylene group include an alkenylene group having from 2 to 6 carbon atoms, such as, for example, ethenylene and butenylene groups.

Examples of the monocyclic cycloalkenylene group can have from 4 to 8 carbon atoms, and include such as, for example, cyclopentenylene and cyclohexenylene groups, and of the polycyclic cycloalkenylene group can have from 5 to 20 carbon atoms, and include such as, for example 7-oxabicyclo[2,2,1]heptenylene and norbornenylene.

Examples of the aralkylene group include such as, for example, benzylidene, tolylene and xylylene groups.

Examples of the aromatic or non-aromatic heterocyclic diradical of 5 to 12 carbons include such as, for example, 3-oxapentane-1,5-diyl, 3-oxacyclohexane-1,4-diyl, 4-azacyclohexane-1,3-diyl, and 4-oxacycloheptane-2,6-diyl.

As used herein, alicyclic diradical means cycloalkylenedialkylene of 7 to 18 carbons and include such as, for example, cyclohexylenedimethylene, cyclopentylenedimethylene and cyclooctylenedimethylene; alkylenedicycloalkylene of 11 to 18 carbons and include such as, for example, 3,3' and 4,4'-methylenebiscyclohexyl and 4,4'-methylenebis(3-methylcyclohexyl); and alkylidenedicycloalkylene of 12 to 18 carbons and include such as, for example, isopropylidenedicyclohexane-4,4'-diyl, ethylidenedicyclohexane-4,4'-diyl and butylidenedicyclooctane-4,4'-diyl.

The alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups are unsubstituted or substituted. Suitable substituents include those which, in the context of this invention, do not alter the properties of the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, such as e.g., a halogen atom (e.g., fluorine, chlorine, bromine, iodine), hydroxy, alkoxy, mercapto, alkylmercapto, nitro, nitroso, cyano, sulfoxy, alkyl, alkoxy such as, for example, methoxy group, ethoxy group, hydroxyethoxy group, propoxy group, hydroxypropoxy group, n-butoxy group, isobutoxy group, sec-butoxy group and t-butoxy group, alkoxycarbonyl such as methoxycarbonyl group and ethoxycarbonyl group, aralkyl such as benzyl group, phenethyl group and cumyl group, acyl such as aralkyloxy group, formyl group, acetyl group, butyryl group, benzoyl group, cinnamyl group and valeryl group, acyloxy such as butyryloxy group, alkenyl, alkenyloxy such as vinyloxy group, propenyloxy group, allyloxy group and butenyloxy group, aryl, aryloxy such as phenoxy group, and aryloxycarbonyl group such as benzoyloxy group.

The invention also relates to a process for forming an image comprising a) coating and baking a substrate with the antireflective coating composition of the present invention; b) coating and baking a photoresist film on top of the antireflective coating; c) imagewise exposing the photoresist; d) developing an image in the photoresist; e) optionally, baking the substrate after the exposing step. The exposed anti-reflective film can then be dry etched, usually in an oxygen-containing plasma, with the photoresist pattern acting as an etch mask.

The polymer comprising a repeating unit selected from formula (I) or (II) can further comprise an additional monomer.

Examples of the additional monomer include, but are not limited to, compounds, which can be optionally substituted, having one addition-polymerizable unsaturated bond selected from an acrylic ester, a methacrylic ester, an acrylamide, a methacrylamide, an allyl compound, a vinyl ether, a vinyl ester, a styrene, a crotonic acid ester, a dialkyl itaconate, a dialkyl ester of maleic acid, a dialkyl ester of fumaric acid, a monoalkyl ester of maleic acid, a monoalkyl ester of fumaric acid, an acrylic acid, a methacrylic acid, a crotonic acid, an itaconic acid, a maleic acid, a fumaric acid, a maleic anhydride, a maleimide, an acrylonitrile, a methacrylonitrile, and a maleonitrile. Examples thereof include, but are not limited to:

acrylic esters such as alkyl acrylate (in certain instances, the alkyl group preferably has from 1 to 10 carbon atoms) (e.g., methyl acrylate, ethyl acrylate, propyl acrylate, t-butyl acrylate, amyl acrylate, cyclohexyl acrylate, ethylhexyl acrylate, octyl acrylate, t-octyl acrylate, chloroethyl acrylate, 2-hydroxyethyl acrylate, 2,2-dimethylhydroxypropyl acrylate, 5-hydroxypentyl acrylate, trimethylolpropane monoacrylate, pentaerythritol monoacrylate, benzyl acrylate, methoxybenzyl acrylate, furfuryl acrylate, tetrahydrofurfuryl acrylate), glycidyl acrylate and aryl acrylate (e.g., phenyl acrylate, hydroxyphenyl acrylate);

methacrylic esters such as alkyl methacrylate (in certain instances, the alkyl group preferably has from 1 to 10 carbon atoms) (e.g., methyl methacrylate, ethyl methacrylate, propyl methacrylate, isopropyl methacrylate, t-butyl methacrylate, amyl methacrylate, allyl methacrylate, hexyl methacrylate, cyclohexyl methacrylate, benzyl methacrylate, chlorobenzyl methacrylate, octyl methacrylate, 2-hydroxyethyl methacrylate, 4-hydroxybutyl methacrylate, 5-hydroxypentyl methacrylate, 2,2-dimethyl-3-hydroxypropyl methacrylate, trimethylol propane monomethacrylate, pentaerythritol monomethacrylate, furfuryl methacrylate, tetrahydrofurfuryl methacrylate), glycidyl methacrylate, and aryl methacrylate (e.g., phenyl methacrylate, hydroxyphenyl methacrylate, cresyl methacrylate, naphthyl methacrylate);

acrylamides such as acrylamide, N-alkylacrylamide (in certain instances, the alkyl group has from 1 to 10 carbon atoms and examples thereof include a methyl group, an ethyl group, a propyl group, a butyl group, a t-butyl group, a heptenyl group, an octyl group, a cyclohexyl group, a benzyl group, a hydroxyethyl group and a benzyl group), N-arylacrylamide (examples of the aryl group include a phenyl group, a tolyl group, a nitrophenyl group, a naphthyl group, a cyanophenyl group, a hydroxyphenyl group and a carboxyphenyl group), N,N-dialkylacrylamide (in certain instances, the alkyl group has from 1 to 10 carbon atoms and examples thereof include a methyl group, an ethyl group, a butyl group, an isobutyl group, an ethylhexyl group and a cyclohexyl group), N,N-arylacrylamide (examples of the aryl group include a phenyl group), N-methyl-N-phenylacrylamide, N-hydroxyethyl-N-methylacrylamide and N-2-acetoamidoethyl-N-acetylacrylamide;

methacrylamides such as methacrylamide, N-alkylmethacrylamide (in certain instances, the alkyl group has from 1 to 10 carbon atoms and examples thereof include a methyl group, an ethyl group, a t-butyl group, an ethylhexyl group, a hydroxyethyl group and a cyclohexyl group), N-arylmethacrylamide (examples of the aryl group include a phenyl group, a hydroxyphenyl group and a carboxyphenyl group), N,N-dialkylmethacrylamide (examples of the alkyl group include an ethyl group, a propyl group and a butyl group), N,N-diarylmethacrylamide (examples of the aryl group include a phenyl group), N-hydroxyethyl-N-methylmethacrylamide, N-methyl-N-phenylmethacrylamide and N-ethyl-N-phenylmethacrylamide;

allyl compounds such as an allyl ester (e.g., allyl acetate, allyl caproate, allyl caprylate, allyl laurate, allyl palmitate, allyl stearate, allyl benzoate, allyl acetoacetate, allyl lactate) and allyloxyethanol;

vinyl ethers such as alkyl vinyl ether (e.g., hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, tetrahydrofurfuryl vinyl ether), vinylaryl ether (e.g., vinylphenyl ether, vinyltolyl ether, vinylchlorophenyl ether, vinyl-2,4-dichlorophenyl ether, vinyinaphthyl ether, vinylanthranyl ether);

vinyl esters such as vinyl butyrate, vinyl isobutyrate, vinyltrimethyl acetate, vinyidiethyl acetate, vinyl valerate, vinyl caproate, vinyl chloroacetate, vinyl dichloroacetate, vinylmethoxy acetate, vinylbutoxy acetate, vinylphenyl acetate, vinyl acetoacetate, vinyl lactate, vinyl-β-phenyl butyrate, vinylcyclohexyl carboxylate, vinyl benzoate, vinyl salicylate, vinyl chlorobenzoate, vinyl tetrachlorobenzoate and vinyl naphthoate;

styrenes such as styrene, alkylstyrene (e.g., methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, acetoxymethylstyrene), alkoxystyrene (e.g., methoxystyrene, 4-methoxy-3-methylstyrene, dimethoxystyrene), halostyrene (e.g., chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, 4-fluoro-3-trifluoromethylstyrene), hydroxystyrene (e.g., 4-hydroxystyrene, 3-hydroxystyrene, 2-hydroxystyrene, 4-hydroxy-3-methylstyrene, 4-hydroxy-3,5-dimethylstyrene, 4-hydroxy-3-methoxystyrene, 4-hydroxy-3-(2-hydroxybenzyl)styrene and carboxystyrene;

crotonic acid esters such as alkyl crotonate (e.g., butyl crotonate, hexyl crotonate, glycerol monocrotonate), dialkyl itaconates (e.g., dimethyl itaconate, diethyl itaconate, dibutyl itaconate);

dialkyl esters of maleic acid or fumaric acid (e.g., dimethyl maleate, dibutyl fumarate) or monoalkyl esters of maleic acid or fumaric acid;

an acrylic acid, a methacrylic acid, a crotonic acid, an itaconic acid, a maleic anhydride, a maleimide, an acrylonitrile, a methacrylonitrile and a maleonitrile. In addition, an addition polymerizable unsaturated compound capable of copolymerization with the repeating structural unit for use in the present invention may also be used.

In general terms, the polymer comprises from about 40 to about 100 mol % when the repeating unit is represented by formula (I) with the balance of about 0 to about 60 mol % being one or more of the additional monomers mentioned above. When the polymer comprises the repeating unit represented by formula (II), the repeating unit represented by formula (II) is generally present in an amount of from about 30 to about 60 mol % with the balance of about 40 to about 70 mol % being one or more of the additional monomers mentioned above.

The polymer which comprises at least one repeating unit selected from formula (I) and formula (II), which can further comprise an additional monomer, can be combined with at least one crosslinking agent to form an antireflective coating composition.

Crosslinking agents are those agents which are capable of forming a crosslinked structure under the action of an acid. Some examples of crosslinking agents include aminoplasts such as, for example, glycoluril-formaldehyde resins, melamine-formaldehyde resins, benzoguanamine-formaldehyde resins, and urea-formaldehyde resins. The use of methylated and/or butylated forms of these resins is highly preferred for obtaining long storage life (3–12 months) in catalyzed form. Highly methylated melamine-formaldehyde resins having degrees of polymerization less than two are useful. Monomeric, methylated glycoluril-formaldehyde resins are useful for preparing thermosetting polyester antireflective coatings which can be used in conjunction with acid-sensitive photoresists. One example is N,N,N,N-tetra(alkoxymethyl)glycoluril. Examples of N,N,N,N-tetra(alkoxymethyl)glycoluril, may include, e.g., N,N,N,N-tetra(methoxymethyl)glycoluril, N,N,N,N-tetra(ethoxymethyl)glycoluril, N,N,N,N-tetra(n-propoxymethyl)glycoluril, N,N,N,N-tetra(i-propoxymethyl)glycoluril, N,N,N,N-tetra(n-butoxymethyl)glycoluril and N,N,N,N-tetra(t-butoxymethyl)glycoluril. N,N,N,N-tetra(methoxymethyl)glycoluril is available under the trademark POWDERLINK from Cytec Industries (e.g., POWDERLINK 1174). Other examples include methylpropyltetramethoxymethyl glycoluril, and methylphenyltetramethoxymethyl glycoluril. Similar materials are also available under the NIKALAC tradename from Sanwa Chemical (Japan).

Other aminoplast crosslinking agents are commercially available from Cytec Industries under the trademark CYMEL and from Monsanto Chemical Co. under the trademark RESIMENE. Condensation products of other amines and amides can also be employed, for example, aldehyde condensates of triazines, diazines, diazoles, guanidines, guanimines and alkyl- and aryl-substituted derivatives of such compounds, including alkyl- and aryl-substituted melamines. Some examples of such compounds are N,N'-dimethyl urea, benzourea, dicyandiamide, formaguanamine, acetoguanamine, ammeline, 2-chloro-4,6-diamino-1,3,5-triazine, 6-methyl-2,4-diamino, 1,3,5-triazine, 3,5-diaminotriazole, triaminopyrimidine, 2-mercapto-4,6-diamino-pyrimidine, 3,4,6-tris(ethylamino)-1,3,5-triazine, tris(alkoxycarbonylamino)triazine, N,N,N',N'-tetramethoxymethylurea, methylolbenzoguanamine or alkyl ether compound thereof, such as tetramethylolbenzoguanamine, tetramethoxymethylbenzoguanamine and trimethoxymethylbenzoguanamine; 2,6-bis(hydroxymethyl)4-methylphenol or alkyl ether compound thereof; 4-tert-butyl-2,6-bis(hydroxymethyl)phenol or alkyl ether compound thereof; 5-ethyl-1,3-bis (hydroxymethyl)perhydro-1,3,5-triazin-2-one (common name: N-ethyldimethyloltriazine) or alkyl ether compound thereof; N,N-dimethyloltrimethyleneurea or dialkyl ether compound thereof; 3,5-bis (hydroxymethyl)perhydro-1,3,5-oxadiazin-4-one (common name: dimethylolurone) or alkyl ether compound thereof; and tetramethylolglyoxazaldiurein or dialkyl ether compound thereof and the like.

Other possible crosslinking agents include: 2,6-bis(hydroxymethyl)-p-cresol and compounds having the following structures:

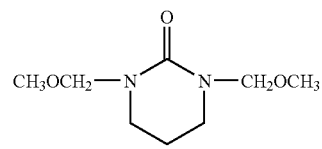

-continued

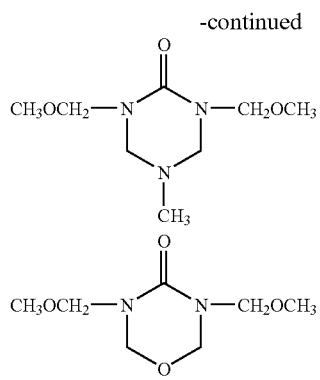

including their analogs and derivatives, such as those found in Japanese Laid-Open Patent Application (Kokai) No. 1-293339 to Tosoh, methylolmelamines, such as hexamethylolmelamine, pentamethylolmelamine, and tetramethylolmelamine as well as etherified amino resins, for example alkoxylated melamine resins (for example, hexamethoxymethylmelamine, pentamethoxymethylmelamine, hexaethoxymethylmelamine, hexabutoxymethylmelamine and tetramethoxymethylmelamine) or methylated/butylated glycolurils, for example as well as those found in Canadian Patent No. 1 204 547 to Ciba Specialty Chemicals. Other examples include, for example, N,N,N,N-tetrahydroxymethylglycoluril, 2,6-dihydroxymethylphenol, 2,2',6,6'-tetrahydroxymethyl-bisphenol A, 1,4-bis[2-(2-hydroxypropyl)] benzene, and the like, etc. Other examples of crosslinking agents include those described in U.S. Pat. No. 4,581,321, U.S. Pat. No. 4,889,789, and DE-A 36 34 371, the contents of which are incorporated by reference. Various melamine and urea resins are commercially available under the Nikalacs (Sanwa Chemical Co.), Plastopal (BASF AG), or Maprenal (Clariant GmbH) tradenames.

Isocyanates can also be used as crosslinking agents and their use, structure and synthesis are well known to those of ordinary skill in the art. Examples of isocyanate crosslinking agents can be found in U.S. Pat. No. 5,733,714, the contents of which are hereby incorporated by reference.

The crosslinking agent can be used individually or in mixtures with each other. The crosslinking agent is added to the composition in a proportion which provides from about 0.10 to about 2.00 equivalents of crosslinking function per reactive group on the polymer.

The antireflective coating composition can further comprise one or more components selected from cross-linking catalysts, solvents, monomeric dyes, surface leveling agents, adhesion promoters, and antifoaming agents.

Cross-linking catalysts include, for example, acid generators, acids, and mixtures thereof. One example of an acid generator is a thermal acid generator. A thermal acid generator is a compound which is not an acid but which is converted to an acid upon heating of the photoresist film. Suitable thermal acid generators useful in the present invention include the ammonium salts of acids where the corresponding amine is volatile. Ammonium salts of acids are prepared by neutralizing an acid with ammonia or an amine. The amine may be a primary, secondary or tertiary amine. The amine must be volatile since it must evaporate from the anti-reflective film upon heating to the temperature required to crosslink the film. When the amine or ammonia evaporates from the anti-reflective film upon heating it leaves an acid in the film. This acid is then present in the anti-reflective film and is employed to catalyze the acid hardening crosslinking reaction upon heating, unless it becomes neutralized by a corresponding amount of a base. Photoacid generators may also be present in the composition and their use and types are well known in the art.

Examples of acid generators include onium salts, benzoin tosylate, nitrobenzyl tosylates, such as 2-nitrobenzyl tosylate, 2,4-dinitrobenzyl tosylate, 2,6-dinitrobenzyl tosylate, 4-nitrobenzyl tosylate; nitrobenzyl benzenesulfonates such as 2-trifluoromethyl-6-nitrobenzyl 4-chlorobenzenesulfonate, as 2-trifluoromethyl-6-nitrobenzyl 4-nitro benzenesulfonate; phenolic sulfonate esters such as phenyl-4-methoxybenzenesulfonate, tris (2,3-dibromopropyl)-1,3,5-triazine-2,4,6-trione, 2,4,4,6-tetrabromocyclohexadienone, the alkyl esters of organic sulfonic acids, p-toluenesulfonic acid, dodecylbenzenesulfonic acid, oxalic acid, phthalic acid, phosphoric acid, camphorsulfonic acid, alkyl and aryl sulfonic acid esters, aromatic sulfonamides, alkyl and aryl phosphoric acid esters, their salts, and mixtures thereof. When benzoin tosylate is heated toluene sulfonic acid is produced by a substitution reaction. Alkyl sulfonates which produce the sulfonic acid by elimination upon heating are examples of other thermal acid generators.

Examples of acids which can be used include the non-salts of the above acid generators and include, for example, organic acids such as sulfonic acids (for example, alkyl and aryl sulfonic acids such as phenylsulfonic acid and para-toluenesulfonic acid), and alkyl and aryl phosphoric acids. One or more cross-linking catalysts can be used in the composition.

Examples of solvents for the coating composition include alcohols, esters, glymes, ethers, glycol ethers, glycol ether esters, ketones, cyclic ketones, and mixtures thereof. Examples of such solvents include, but are not limited to, propylene glycol methyl ether, propylene glycol methyl ether acetate, cyclohexanone, 2-heptanone, ethyl 3-ethoxypropionate, propylene glycol methyl ether acetate, ethyl lactate, and methyl 3-methoxypropionate. The solvent is typically present in an amount of from about 40 to about 95 weight percent.

Since the composition is coated on top of the substrate and is further subjected to dry etching, it is envisioned that the composition is of sufficiently low metal ion level and purity that the properties of the semiconductor device are not adversely affected. Treatments such as passing a solution of the polymer, or compositions containing such polymers, through an ion exchange column, filtration, and extraction processes can be used to reduce the concentration of metal ions and to reduce particles.

The coating composition can be coated on the substrate using techniques well known to those skilled in the art, such as dipping, spincoating or spraying. The film thickness of the anti-reflective coating ranges from about 0.01 μm to about 1 μm. The coating can be heated on a hot plate or convection oven or other well known heating methods to remove any residual solvent and induce crosslinking if desired, and insolubilizing the anti-reflective coatings to prevent intermixing between the anti-reflective coating and the photoresist.

There are two types of photoresist compositions, negative-working and positive-working. When negative-working photoresist compositions are exposed image-wise to radiation, the areas of the resist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating, thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying surface is uncovered.

Negative working photoresist and positive working photoresist compositions and their use are well known to those skilled in the art.

A process of the instant invention comprises coating a substrate with a coating composition comprising a polymer of the present invention and heating the substrate on a hotplate or convection oven or other well known heating methods at a sufficient temperature for sufficient length of time to remove the coating solvent, and crosslink the polymer if necessary, to a sufficient extent so that the coating is not soluble in the coating solution of a photoresist or in a aqueous alkaline developer. An edge bead remover may be applied to clean the edges of the substrate using processes well known in the art. The heating ranges in temperature from about 70° C. to about 250° C. If the temperature is below 70° C. then insufficient loss of solvent or insufficient amount of crosslinking may take place, and at temperatures above 250° C., the polymer may become chemically unstable. A film of a photoresist composition is then coated on top of the anti-reflective coating and baked to substantially remove the photoresist solvent. The photoresist is image-wise exposed and developed in an aqueous developer to remove the treated resist. An optional heating step can be incorporated into the process prior to development and after exposure. The process of coating and imaging photoresists is well known to those skilled in the art and is optimized for the specific type of resist used. The patterned substrate can then be dry etched in a suitable etch chamber to remove the exposed portions of the anti-reflective film, with the remaining photoresist acting as an etch mask.

The invention also relates to a compound having the formula

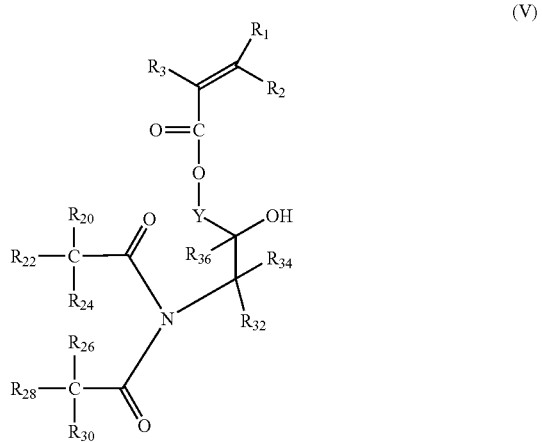

(V)

where $R_1$, $R_2$, and $R_3$ are each independently selected from hydrogen or alkyl; $R_7$ is alkyl or aryl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

The compound is generally made by reacting a compound of formula (IB)

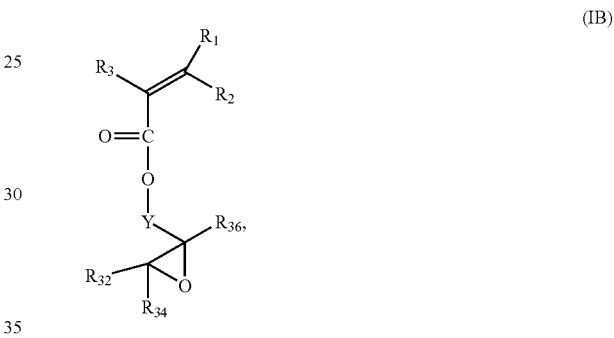

(IB)

where $R_1$, $R_2$, and $R_3$ are each independently selected from hydrogen or alkyl; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, carbocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted, with a compound of formula (IA)

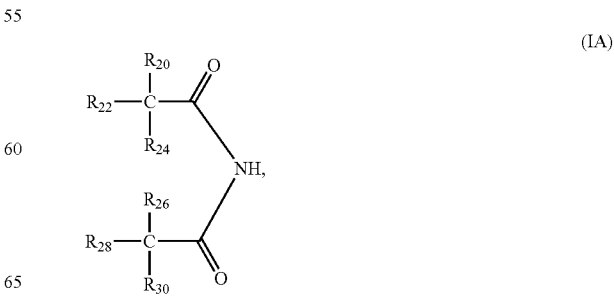

(IA)

where $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, or $R_{24}$ and $R_{26}$ taken together (i) form a direct bond, (ii) form —$(CH_2)_{n1}(O)_{n2}(CH_2)_{n3}$— where n2 is 0 or 1 and n1+n2+n3=1 to 5, or (iii) with the carbon atoms to which they are attached form a carbocyclic ring and $R_{20}$, $R_{22}$, $R_{28}$ and $R_{30}$ are as defined above, the alkyl, aryl, aralkyl, heterocyclic ring, and carbocyclic ring being unsubstituted or substituted, together in the presence of a catalyst, for example, benzyltriethylamine chloride, in a solvent (for example, cyclohexanone) with stirring for from about 5 to about 48 hours at a temperature of from about 80 to about 145° C. For example, compounds of formula (IA) include succinimide, glutarimide, 3,5-morpholinedione, phthalimide, and naphthalimide.

The compound of formula (IB) can be made generally by reacting (IB-1) with (IB-2) under normal conditions known to those of ordinary skill in the art

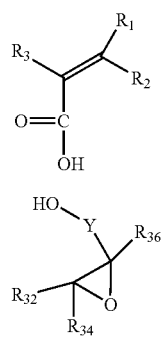

(IB-1)

(IB-2)

For example, in the case where $R_1$ and $R_2$ are hydrogen and $R^3$ is methyl for (IB-1) and Y is methylene and $R_{32}$, $R_{34}$, and $R_{36}$ are hydrogen for (IB-2), reacting under normal conditions known to those of ordinary skill in the art yields glycidyl methacrylate.

In addition, the invention also relates to reacting a vinyl polymer or copoylymer which has from about 40 to about 100 mol % of an epoxy substituent with an imide in the presence of a catalyst and solvent similar to that used above. See Scheme I below.

Scheme I

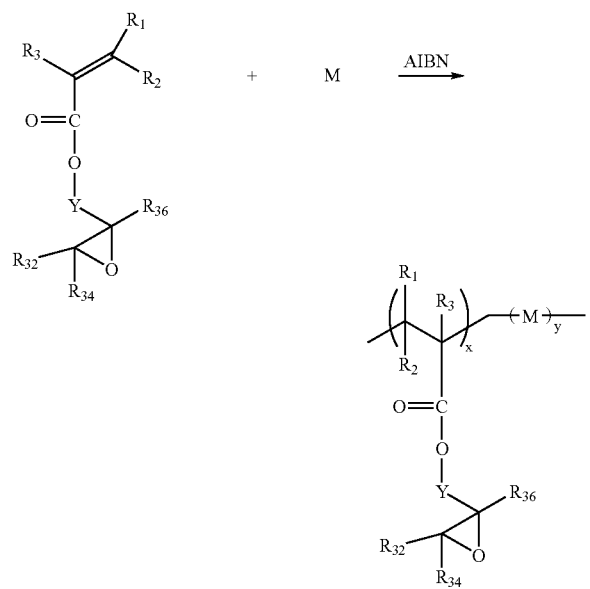

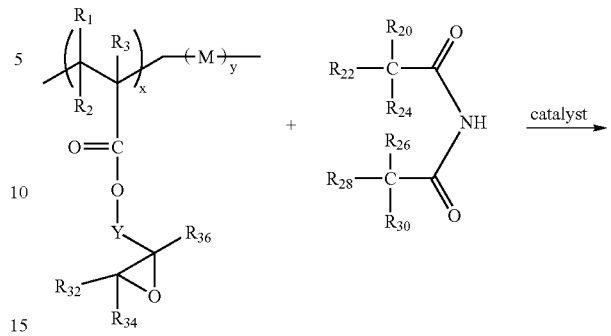

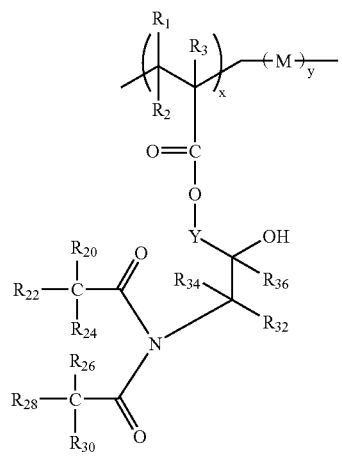

For example, an acrylic copolymer comprising about 40 to about 100% of, for example, formula (IV) is prepared in the normal fashion (reacting for example two monomers (one monomer being compound of formula (IB) where Y is methylene and $R_{32}$, $R_{34}$, and $R_{36}$ are hydrogen and monomer M) in the presence of azobisisobutyronitrile in a solvent, for example, cyclohexanone). The resulting polymer (IV) is then reacted with an imide, for example, a compound of formula (IA), for example, succinimide (in an amount equal to the moles of epoxy units in the copolymer), in the presence of a catalyst. See Scheme II below. The resulting polymer (formula (X)) can then be used to make antireflective coating compositions.

Scheme II

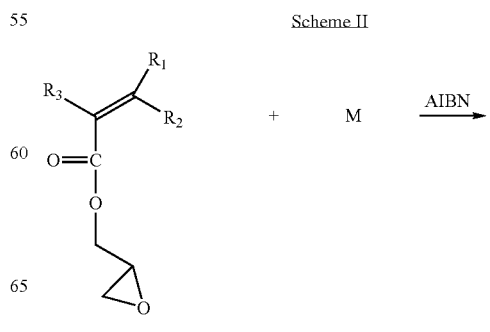

-continued

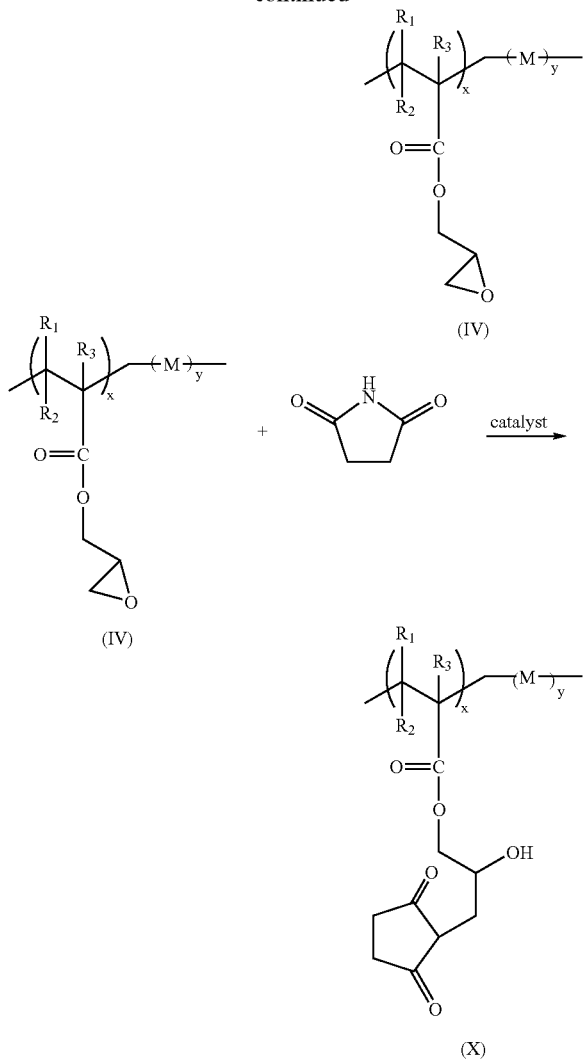

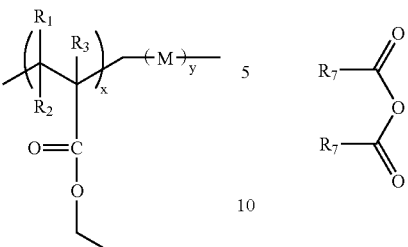

where M is an additional monomer and $R_1$, $R_2$, and $R_3$ are as described hereinabove.

The invention also relates to making a compound having formula (III) comprising

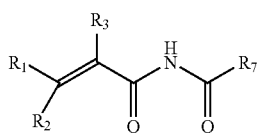
(III)

reacting a compound having formula (IIIa) with a compound having formula (IIIb)

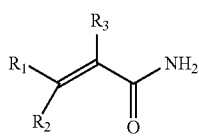
(IIIa)

(IIIb)

where $R_1$, $R_2$, and $R_3$ are each independently selected from hydrogen or alkyl; and $R_7$ is alkyl or aryl, in the presence of a catalyst and separating the compound of formula (III) from the reaction mixture.

The following examples provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

Example 1

Succinimide-Glycidyl Methacrylate (GMA) Adduct 22.7 g (0.16 mol) of glycidyl methacrylate, 15.5 g (0.16 mol) of succinimide and 1.0 g (4.0 mmol) of benzyltriethylamine chloride were placed into a suitably sized reaction vessel fitted with a stirrer and a nitrogen gas source. 200 g of cyclohexanone were added to dissolve the materials. The mixture was stirred at a temperature of about 105 to about 120° C. for 24 hours until the reaction was completed. The reaction yielded 238 g in total amount of solution, which contained 16 wt % of the succinimide-GMA adduct.

Example 2

Copolymerization of Succinimide-GMA Adduct with Benzyl Methacrylate 44 g (0.030 mol) of the succinimide-GMA Adduct from Example 1 was placed into a suitably sized reaction vessel fitted with a stirrer and a nitrogen gas source. 1.76 g (0.010 mol) of benzyl methacrylate in 50 g of propylene glycol monomethyl ether acetate was added to the vessel. The mixture was heated to about 70° C., 0.45 g of azobisisobutyronitrile was added under a nitrogen blanket and the polymerization reaction was allowed to proceed for about 20 hours. The mixture was allowed to cool to room temperature and the reaction mixture was precipitated in ethyl ether. A light-yellow polymer solid precipitated. The light-yellow polymer solid was re-precipitated in deionized water and dried in vacuo at 45° C. Yield was 8.8 g (98%).

Example 3

Preparation of Anti-Reflective Coating Composition 1.50 g of the polymer solid from Example 2 was dissolved in 48.5 g of propylene glycol monomethyl ether to make a 3.0 wt % solution. 0.3 g of a glycoluril crosslinking agent, 0.3 g of a 10% solution of para-toluene sulfonic acid triethylamine salt in ethyl lactate, and 0.015 g of a photoacid generator were mixed into the polymer solution with stirring. The mixture then was filtered through a micro filter with a pore size of 0.2 µm.

Example 4

Performance of Anti-Reflective Coating Composition

The composition of Example 3 was spin-coated on a silicon wafer for 40 seconds. The wafer was heated on a hot-plate at 200° C. for 1 minute. The film thickness was determined to be 0.10 µm. The antireflective coating was subjected to analysis with spectroscopic ellipsometer. The optimized reflective index "n" at 193 nm was 1.75 and the absorption parameter "k" was 0.34.

Example 5

Preparation of Anti-Reflective Coating Composition

An antireflective coating composition was made by dissolving 1.467 g of the polymer solid from Example 2, 0.365 g of a glycoluril crosslinking agent and 0.29 g of a 10% solution of para-toluene sulfonic acid triethylamine salt in 24.69 g propylene glycol monomethylether acetate and 10.58 g propylene glycol monomethylether with stirring. The mixture then was filtered through a micro filter with a pore size of 0.2 µm.

Example 6

Performance of Anti-Reflective Coating Composition

The composition of Example 5 was spin-coated onto an 8" silicon wafer at ~3000 rpm for 40 seconds. The wafer was heated on a hot-plate at 200° C. for 1 minute. The film thickness was determined to be 0.10 µm. The antireflective coating was subjected to analysis with spectroscopic ellipsometer (J. A. Woollam VUV-Vase Ellipsometer, Model #VU-302). The optimized reflective index "n" at 193 nm was 1.74 and the absorption parameter "k" was 0.33.

Example 7

Copolymerization of Succinimide-GMA Adduct with Styrene 44 g (0.030 mol) of the succinimide-GMA Adduct from Example 1 was placed into a suitably sized reaction vessel fitted with a stirrer and nitrogen gas source. 0.83 g (0.008 mol) of styrene in 40 g of propylene glycol monomethyl ether acetate was added to the vessel. The mixture was heated to about 70° C., 0.4 g of azobisisobutyronitrile was added and the polymerization reaction was allowed to proceed for 20 hours. The reaction mixture was allowed to cool down to room temperature.

Example 8

Preparation of Anti-Reflective Coating Composition 12 g of the polymer solution (9.5% polymer solid) from Example 7 was added to 24.0 g of propylene glycol monomethyl ether acetate to make a 3.2 wt % solution. 0.23 g of a glycoluril crosslinking agent, 0.23 g of a 10% solution of para-toluene sulfonic acid triethylamine salt in ethyl lactate, and 0.012 g of a photoacid generator were mixed into the polymer solution. The mixture then was filtered through a micro filter with a pore size of 0.2 µm.

Example 9

Performance of Anti-Reflective Coating Composition

The composition of Example 8 was spin-coated on a silicon wafer for 40 seconds. The wafer was heated on a hot-plate at 200° C. for 1 minute. The film thickness was determined to be 0.094 µm. The antireflective coating was subjected to analysis with spectroscopic ellipsometer. The optimized reflective index "n" at 193 nm was 1.65 and the absorption parameter "k" was 0.32.

Example 10

Synthesis of N-acetyl Acrylamide 71.0 g (0.50 mol) of acrylamide was placed in a suitably sized reaction vessel fitted with a stirrer and nitrogen gas source. To the vessel was added in 204 g of acetic anhydride and the mixture was heated to 80° C. Amberlite 15 cation exchange resin (Rohm & Haas) was added to the vessel and the mixture was heated to ~100 to 110° C. After 2 hours, the cation exchange resin was removed by filtration and acetic acid was taken off by evaporation. A white solid was precipitated and collected. The crude product was recrystallized from minimum methanol and washed with cold ether. The reaction yielded 37 g (65%) of N-acetyl acrylamide.

Example 11

Copolymerization of N-acetyl Acrylamide with 2-hydroxyethyl Methacrylate and Benzyl Methacrylate 3.6 g (0.032 mol) of N-acetyl acrylamide from Example 10, 2.3 g (0.013 mol) of benzyl methacrylate and 2.54 g (0.020 mol) of 2-hydroxyethyl methacrylate were placed in a suitably sized reaction vessel fitted with a stirrer and nitrogen gas source. To the vessel was added 50 ml of methanol. The mixture was heated to reflux (65–70° C.) under nitrogen in the presence of 0.16 g azobisisobutyronitrile. The reaction was allowed to proceed for 12 hours. The polymer solution was precipitated in ethyl ether. A white solid precipitated, was re-precipitated in ethyl ether and collected to give 8.3 g (98%) of polymer product.

Example 12

Preparation of Anti-Reflective Coating Composition 1.50 g of the polymer solid from Example 11 was dissolved in 48.5 g of ethyl lactate to make a 3.0 wt % solution. 0.3 g of a glycoluril crosslinking agent, and 0.3 g of a 10% solution of para-toluene sulfonic acid triethylamine salt in ethyl lactate were mixed into the polymer solution. The mixture then was filtered through a micro filter with a pore size of 0.2 µm.

Example 13

Performance of Anti-Reflective Coating Composition

The composition of Example 12 was spin-coated on a silicon wafer for 40 seconds. The wafer was heated on a hot-plate at 200° C. for 1 minute. The film thickness was determined to be 0.10 μm. The antireflective film coated on the silicon wafer gave a value of reflective index "n" of 1.73 and optical absorbance factor "k" of 0.35.

Example 14

Lithography Performance

The lithographic performance of the composition of Example 3 was evaluated using AZ® EXP AX1120P resist (Clariant Corporation, AZ Electronic Materials, Somerville, N.J.). A silicon wafer was coated with about an 87 nm thick film of the anti-reflective coating composition of Example 3 and baked at 200° C. for 60 seconds. Then a 330 nm thick AZ® EXP AX1120P resist solution was coated on top of the anti-reflective coating and baked at 130° C. for 60 seconds. The coated wafer was then imagewise exposed using an ISI 193 nm mini-stepper with 0.60 NA, under ⅔ annular illumination of 0.42/0.70 sigma with binary mask. The exposed wafer was baked at 130° C. for 60 seconds and developed using a 2.38 wt % aqueous solution of tetramethyl ammonium hydroxide for 60 seconds. At exposure dose of 28 mJ, the line and space patterns at 0.12 μm 1:1 pitch were observed under scanning electron microscope and showed no standing waves indicating the efficacy of the bottom anti-reflective coating. The depth of focus for above patterns at above dose was greater than 0.60 μm.

Example 15

Lithographic Performance

The lithographic performance of the composition of Example 5 was evaluated using AZ® EXP AX1120P resist (product of AZ Electronic Materials, Clariant Corporation, Somerville, N.J.). A silicon wafer was coated with about an 87 nm thick film of the anti-reflective coating composition of Example 5 and baked at 200° C. for 60 seconds. Then a 270 nm thick AZ® EXP AX 120P resist solution was coated and baked at 130° C. for 60 seconds. The wafer was then imagewise exposed using a Nikon NSR-S306c Scanner with 0.78NA, under ⅔ annular illumination of 0.56/0.85 sigma with 6% HTPSM mask. The exposed wafer was baked at 130° C. for 60 seconds and developed using a 2.38 wt % aqueous solution of tetramethyl ammonium hydroxide for 60 seconds. At exposure dose of 35 mJ, the line and space patterns at 90 nm 1:1 Pitch were observed under scanning electron microscope and showed no standing waves indicating the efficacy of the bottom anti-reflective coating. The depth of focus for above patterns at above dose was greater than 0.35 μm.

Example 16

Lithography Performance

The lithographic performance of the composition of Example 12 was evaluated using AZ® EXP AX1120P resist (Clariant Corporation, AZ Electronic Materials, Somerville, N.J.). A silicon wafer was coated with about an 88 nm thick film of the anti-reflective coating composition of Example 3 and baked at 200° C. for 60 seconds. Then a 330 nm thick AZ® EXP AX1120P resist solution was coated on top of the anti-reflective coating and baked at 130° C. for 60 seconds. The wafer was then imagewise exposed using an ISI 193 nm mini-stepper with 0.60 NA, under ⅔ annular illumination of 0.42/0.70 sigma with binary mask. The exposed wafer was baked at 130° C. for 60 seconds and developed using a 2.38 wt % aqueous solution of tetramethyl ammonium hydroxide for 60 seconds. At exposure dose of 30 mJ, the line and space patterns at 0.12 μm 1:1 pitch were observed under scanning electron microscope and showed no standing waves indicating the efficacy of the bottom anti-reflective coating. The depth of focus for above patterns at above dose was greater than 0.45 μm.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. A polymer comprising at least one repeating unit represented by formula (I)

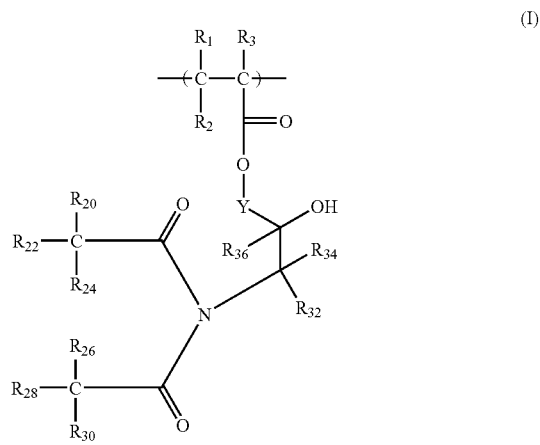

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

2. The polymer of claim 1 which further comprises an additional monomer.

3. The polymer of claim 2 wherein the additional monomer is selected from optionally substituted acrylic esters, optionally substituted acrylic acids, optionally substituted methacrylic esters, optionally substituted methacrylic acids, optionally substituted acrylamides, optionally substituted methacrylamides, optionally substituted allyl compounds, optionally substituted styrenes, optionally substituted hydroxystyrene, optionally substituted hydroxyisopropylstyrene, optionally substituted methylstyrene, optionally substituted hydroxymethylstyrene, optionally substituted hydroxyl-α-methylstyrene, optionally substituted vinyl ethers, optionally substituted vinyl esters, optionally substituted crotonic acids, optionally substituted crotonic acid esters, optionally substituted maleic anhydride, optionally substituted dialkyl itaconates, optionally substituted monoalkyl or dialkyl esters of maleic acid or fumaric acid, and mixtures thereof.

4. The polymer of claim 3 wherein the additional monomer is selected from optionally substituted methacrylic esters and optionally substituted styrenes.

5. The polymer of claim 4 wherein the methacrylic esters contains a pendent hydroxyl group.

6. The polymer of claim 1 wherein Y is linear or branched alkylene.

7. The polymer of claim 6 wherein each of $R_{32}$, $R_{34}$, and $R_{36}$ are independently hydrogen.

8. A compound having the formula

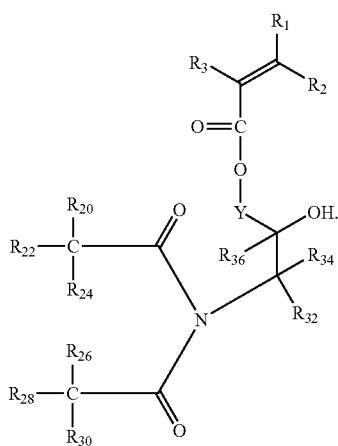

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted.

9. The compound of claim 8 wherein Y is linear or branched alkylene.

10. The compound of claim 8 wherein each of $R_{32}$, $R_{34}$, and $R_{36}$ are independently hydrogen.

11. An antireflective coating composition comprising:
   a) a polymer comprising at least one repeating unit represented by formula (I)

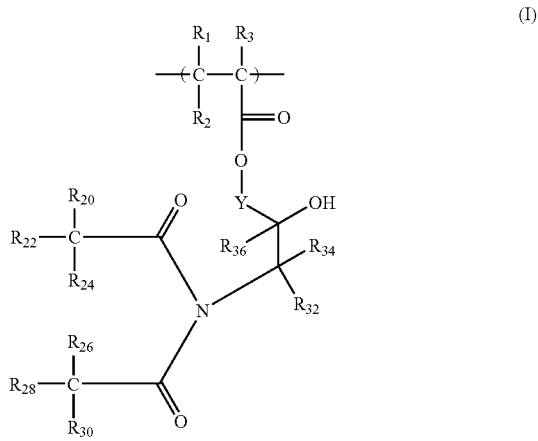

where $R_1$, $R_2$, and $R_3$ are each independently selected from hydrogen or alkyl; $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted; and
   b) at least one crosslinking agent.

12. The composition of claim 11 wherein for a), the polymer further comprises an additional monomer.

13. The composition of claim 12 wherein the additional monomer is selected from optionally substituted acrylic esters, optionally substituted acrylic acids, optionally substituted methacrylic esters, optionally substituted methacrylic acids, optionally substituted acrylamides, optionally substituted methacrylamides, optionally substituted allyl compounds, optionally substituted styrenes, optionally substituted hydroxystyrene, optionally substituted hydroxyisopropylstyrene, optionally substituted methylstyrene, optionally substituted hydroxymethylstyrene, optionally substituted hydroxyl-α-methylstyrene, optionally substituted vinyl ethers, optionally substituted vinyl esters, optionally substituted crotonic acids, optionally substituted crotonic acid esters, optionally substituted maleic anhydride, optionally substituted dialkyl itaconates, optionally substituted monoalkyl or dialkyl esters of maleic acid or fumaric acid, and mixtures thereof.

14. The composition of claim 12 wherein the additional monomer is selected from optionally substituted methacrylates and optionally substituted styrenes.

15. The composition of claim 14 wherein the methacrylic esters contains a pendent hydroxyl group.

16. The composition of claim 11 wherein for a), Y is linear or branched alkylene.

17. The composition of claim 11 wherein for a), each of $R_{32}$, $R_{34}$, and $R_{36}$ are independently hydrogen.

18. The composition of claim 11 wherein b) the crosslinking agent is selected from aminoplasts, isocyanates and mixtures thereof.

19. The composition of claim 11 which further comprises at least one additional component selected from solvents, cross-linking catalysts, monomeric dyes, surface leveling agents, adhesion promoters, and antifoaming agents.

20. A method of making the compound of claim 8 comprising reacting a compound of formula (IB)

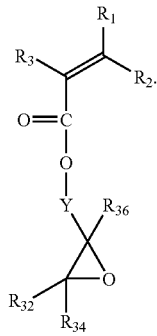

(IB)

where $R_1$, $R_2$, and $R_3$ are each independently selected from hydrogen or alkyl; $R_{32}$, $R_{34}$, and $R_{36}$ are independently selected from hydrogen, alkyl, aryl, aralkyl, or 5-, 6-, or 7-membered heterocyclic ring containing at least one heteroatom selected from nitrogen, oxygen or sulfur; and Y is selected from linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical groups, the alkyl, aryl, aralkyl, heterocyclic ring, linear or branched alkylene, monocyclic or polycyclic alkylene, arylene, aralkylene, polyoxyalkylene, linear or branched alkenylene, monocyclic or polycyclic alkenylene, aromatic or non-aromatic heterocyclic diradical and alicyclic diradical being unsubstituted or substituted, with a compound of formula (IA)

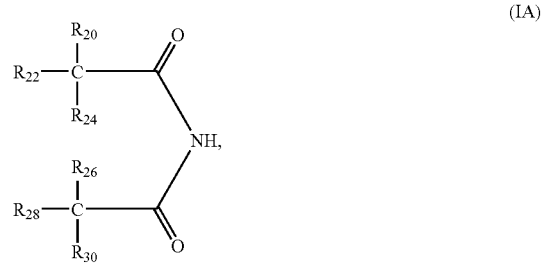

(IA)

where $R_{20}$, $R_{22}$, $R_{24}$, $R_{26}$, $R_{28}$, and $R_{30}$ are independently selected from hydrogen, alkyl, aryl, aralkyl, or 5-, 6-, or 7-membered heterocyclic ring containing at least one heteroatom selected from nitrogen, oxygen or sulfur, the alkyl, aryl, aralkyl, and heterocyclic ring, being unsubstituted or substituted, in the presence of a catalyst and separating the compound of claim 8 from the reaction mixture.

21. The method of claim 20 wherein Y is linear or branched alkylene.

22. The method of claim 20 wherein each of $R_{32}$, $R_{34}$, and $R_{36}$ are independently hydrogen.

* * * * *